(12) United States Patent
Berge

(10) Patent No.: US 6,353,956 B1
(45) Date of Patent: Mar. 12, 2002

(54) COMBINED ULTRASONIC TOOTHBRUSH MODULE

(76) Inventor: Jason Berge, 11613 NE. 90th St., Kirkland, WA (US) 98033

(*) Notice: Subject to any disclaimer, the term of this patent is extended or adjusted under 35 U.S.C. 154(b) by 0 days.

(21) Appl. No.: 09/652,944

(22) Filed: Aug. 31, 2000

Related U.S. Application Data
(60) Provisional application No. 60/152,486, filed on Sep. 3, 1999.

(51) Int. Cl.[7] .......................... A46B 13/02; A61C 17/20
(52) U.S. Cl. ........................................ 15/22.1; 15/167.2
(58) Field of Search ................................ 15/22.1, 22.2, 15/105, 167.2

(56) References Cited

U.S. PATENT DOCUMENTS

| 4,127,125 | A | | 11/1978 | Takemoto et al. |
| 4,237,574 | A | * | 12/1980 | Kelly et al. |
| 4,244,373 | A | | 1/1981 | Nachman |
| 5,072,481 | A | * | 12/1991 | Weyer |
| 5,175,901 | A | * | 1/1993 | Rabinowitz |
| 5,263,218 | A | * | 11/1993 | Guiliani et al. |
| 5,311,632 | A | * | 5/1994 | Center |
| 5,330,357 | A | | 7/1994 | Keller |
| 5,337,435 | A | * | 8/1994 | Krasner et al. |
| 5,365,624 | A | * | 11/1994 | Berns |
| 5,369,831 | A | * | 12/1994 | Bock |
| 5,378,153 | A | * | 1/1995 | Guiliani et al. |
| 5,496,256 | A | | 3/1996 | Bock et al. |

* cited by examiner

Primary Examiner—Terrence R. Till
(74) Attorney, Agent, or Firm—Dean A. Craine

(57) ABSTRACT

A U-shaped, ultrasonic toothbrush module to be used with currently available ultrasonic toothbrush hand pieces made of soft thermoplastic, silicone, or latex material with upper and lower bridge receiving spaces formed on opposite sides. The receiving spaces are designed to receive a user's upper and lower bridges when placed into the user's mouth. Disposed on the three inside surfaces of each receiving space are a plurality of bristles which completely contact the exposed surfaces of every tooth when the device is used. The module includes a housing with a pivoting T-shaped member and magnets attached at one end that connects to a standard ultrasonic toothbrush hand piece. Motion generated by the hand piece is transmitted through the T-shaped member and to the U-shaped member. The movement of the U-shaped member generates ultrasonic waves that are transmitted to the surfaces of the teeth and move the brushes when teeth are placed into the upper and lower bridge receiving spaces.

8 Claims, 4 Drawing Sheets

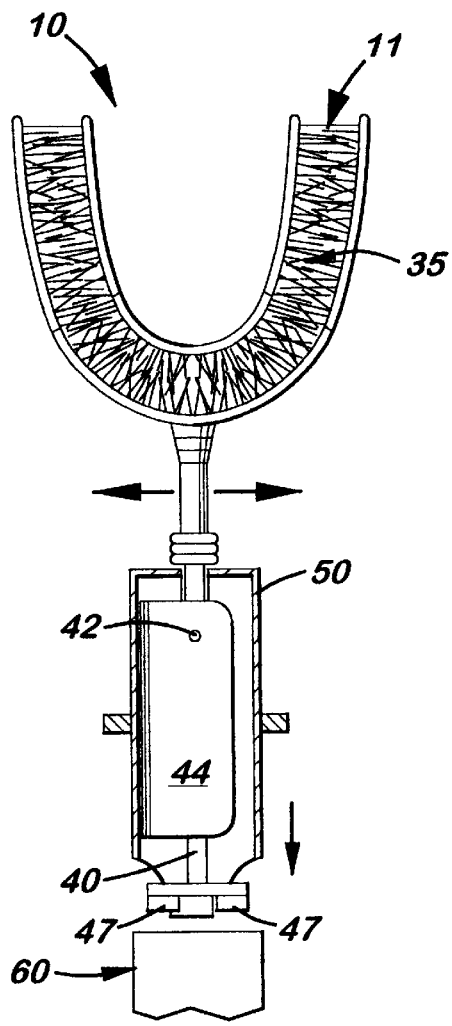
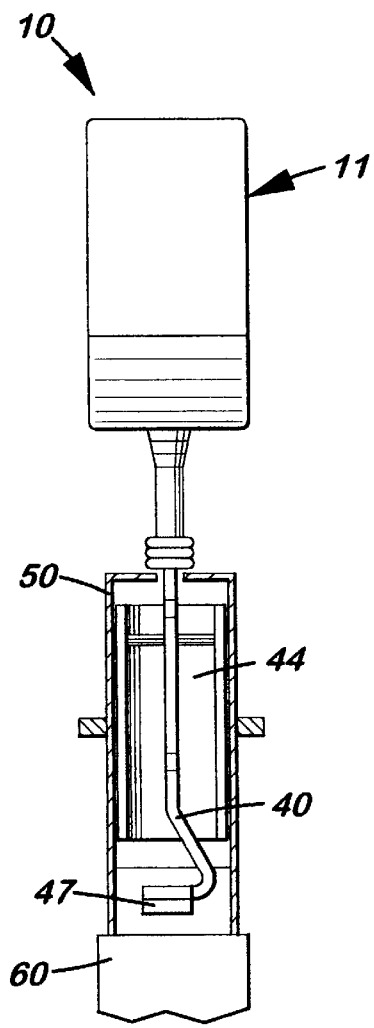
*FIG. 3*
*FIG. 4*
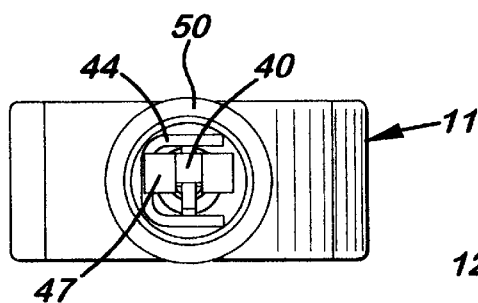
*FIG. 5*
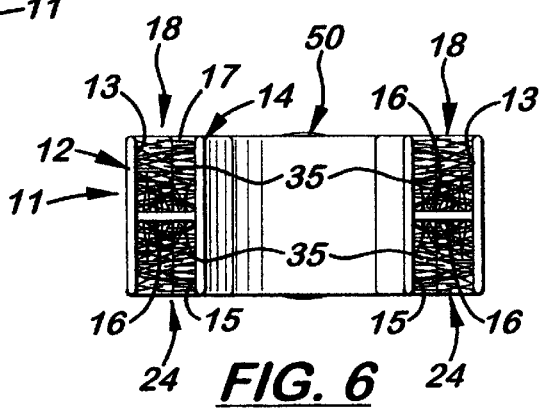
*FIG. 6*

COMBINED ULTRASONIC TOOTHBRUSH
MODULE

This is a utility patent application based on a provisional patent application (Ser. No. 60/152,486) filed on Sep. 3, 1999.

BACKGROUND OF THE INVENTION

1. Field of the Invention

This invention relates to toothbrushes and more particularly, to toothbrushes designed to simultaneously clean a large number of teeth using ultrasonic waves.

2. Description of the Related Art

It is well known that tooth brushing is required for good dental hygiene. Ideally, every tooth in the mouth should be brushed on every surface above the gums. Usually, the bristles of the toothbrush are moved up and down over the exposed tooth surfaces and are worked into the spaces between the teeth and into the gum pockets. For most individuals, the entire tooth brushing process takes two to three minutes. Unfortunately, many individuals do not use proper technique nor spend an adequate amount of time brushing.

Recently, toothbrushes and other dental appliances have been developed that use ultrasonic waves to clean teeth. While such devices, if used properly, appear to adequately clean teeth, their efficacy is also dependent on the user's ability to brush properly for a sufficient amount of time.

U.S. Pat. No. 4,127,125 (Takemoto, et al.) discloses a device for transmitting ultrasonic waves to teeth comprising a mouth-guard structure filled with an ultrasonic wave-transmitting medium. During use, the structure is placed in the mouth so that the teeth of the upper and lower bridges are simultaneously disposed into the U-shaped upper and lower teeth receiving passages formed on the structure. The structure is attached to a hand piece capable of generating ultrasonic waves in the ultrasonic wave medium. Fluoride or other suitable decay-retarding agents may be applied to the top and bottom passages to provide protection against cavities. Unfortunately, such devices do not include means to clean the surfaces of the teeth, nor the spaces between the teeth or the gum pockets.

SUMMARY OF THE INVENTION

It is an object of the present invention to provide a device that can be used to simultaneously clean every tooth in an individual's mouth.

It is another object of the present invention to provide such a device that uses both bristles and ultrasonic wave action to clean teeth.

It is a further object of the present invention to provide such a device that is selectively attachable for use with currently available ultrasonic toothbrushes.

These and other objects are met by an improved teeth-cleaning module shown and described herein. The module comprises a U-shaped member made of soft, biocompatible thermoplastic, silicone, or latex material with complimentary shaped outer and inner U-shaped elements. The inner U-shaped element is aligned inside and spaced apart from the outer U-shaped element thereby forming opposite upper and lower bridge receiving spaces. The upper and lower bridge receiving spaces are designed to receive a user's upper and lower bridges, respectively, when the U-shaped member is placed into the user's mouth. Attached to the inside surfaces of the outer and inner U-shaped elements and extending into the bridge receiving spaces are a plurality of bristles which, during use, contact the surfaces of the teeth and gums.

The module includes means for connecting the U-shaped member to vibration producing means that can be connected to an ultrasonic toothbrush piece commonly used in the prior art and incorporated herein. In one embodiment, the means comprises a single stem disposed between the hand piece and the forward, outer edge of the U-shaped member. In another embodiment, the means comprises a Y-shaped yoke member with a central leg that connects to the member that extends from the vibration producing means. The two opposite legs of the Y-shaped yoke member wrap around the sides of the U-shaped member.

During use, the hand piece causes the vibration producing means to vibrate and create ultrasonic waves that are transmitted through the U-shaped member to the surfaces of the teeth. As the U-shaped member vibrates, the bristles move across the surfaces of the teeth, between the teeth, and into the gum pockets to provide enhanced cleaning action. The vibration producing means is assembled in an outer housing that connects to various dental ultrasonic hand pieces currently available today. By designing the module to be used with such hand pieces, the module may be used as an adjunct to the other brush head modules.

BRIEF DESCRIPTION OF THE DRAWINGS

FIG. 3 is a top plan view of the invention showing the outer housing partially removed.

FIG. 4 is a side elevational view of the invention similar to the FIG. 3.

FIG. 5 is a rear side elevational view of the invention.

FIG. 6 is a front elevational view of the invention.

DESCRIPTION OF THE PREFERRED EMBODIMENT(S)

Figure 1:
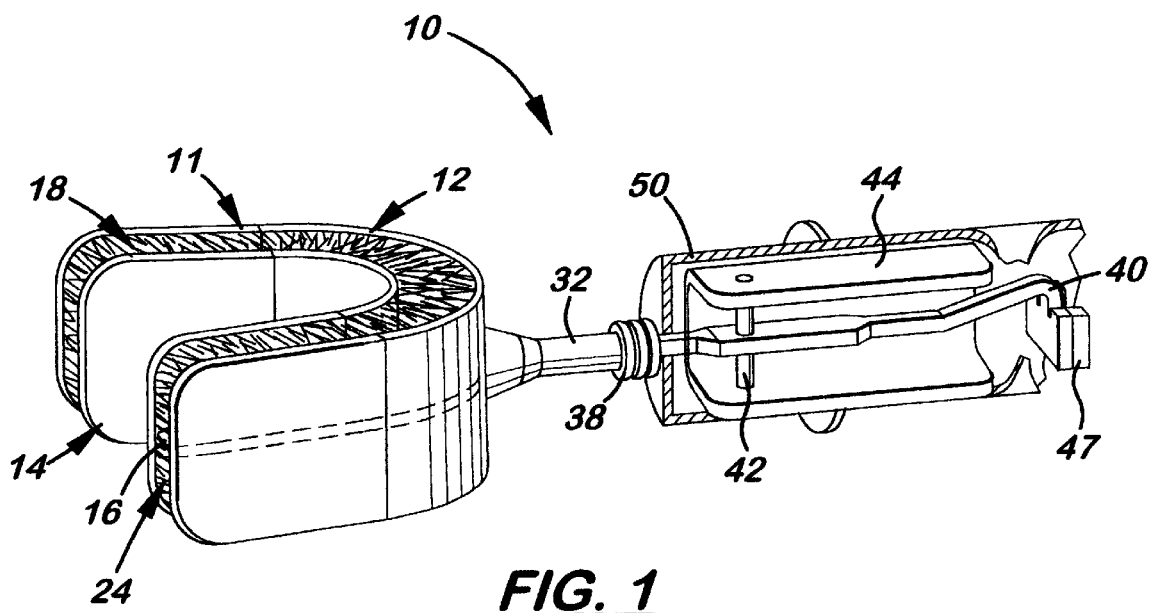
FIG. 1 is a perspective view of the combination ultrasonic toothbrush module disclosed herein.
Figure 2:
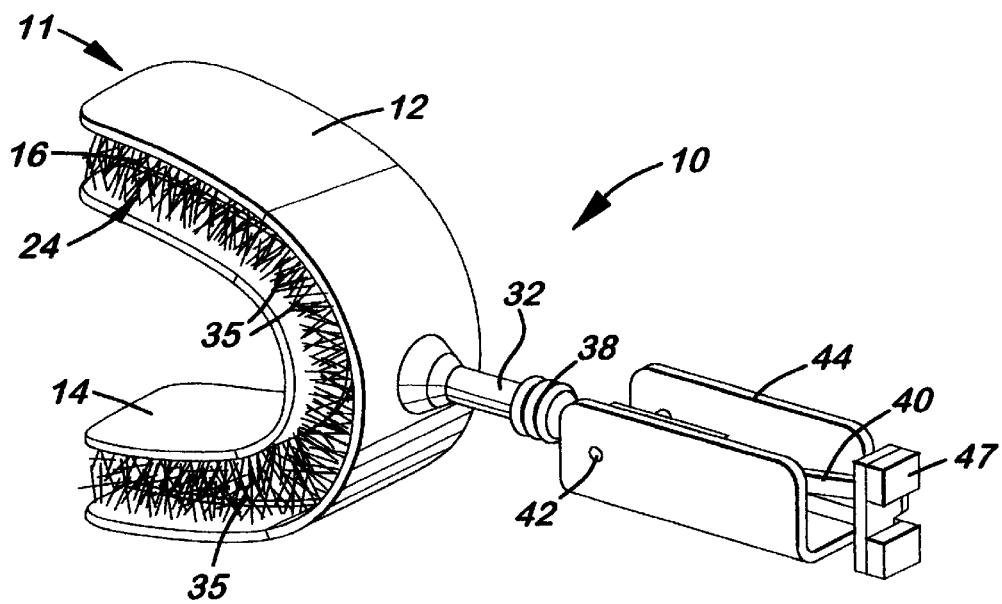
FIG. 2 is another perspective view of the invention shown in FIG. 1 showing the outer housing removed.

Referring to the accompanying Figs., wherein like reference numbers refer to like components, there is shown an improved teeth-cleaning module, generally referred to as 10, designed to be used with currently available ultrasonic toothbrush products. The module 10 comprises a U-shaped member 11 made of soft, biologically safe, thermoplastic, silicone, or latex material with upper and lower bridge receiving spaces, 18, 24, respectively, formed on opposite sides thereof. More specifically, the U-shaped member 11 comprises two complementary-shaped outer and inner U-shaped elements 12, 14, respectively. The inner U-shaped element 14 is aligned inside and spaced apart from the outer U-shaped member 12 thereby forming opposite upper and lower bridge receiving spaces 18, 24, respectively. The bridge receiving spaces 18, 24, are designed to receive a user's upper and lower bridges when the U-shaped member 11 is placed into the user's mouth. Disposed continuously around the U-shaped member 11 and between the outer and inner U-shaped elements 12, 14 is a centrally aligned flange member 16.

Disposed inside the bridge receiving spaces 18, 24, is a plurality of inward extending bristles 35. In the embodiment shown in FIGS. 1–6, the bristles 35 are evenly distributed on the inside surfaces, 13, 15 of each U-shaped element 12, 14, and on the top surface 17 and bottom surface (not shown) of the flange member 16. In the embodiment shown in FIGS. 7–11, the bristles 35 are gathered in tufts and attached to the inside surfaces of the outer and inner U-shaped elements 12, 14. In both embodiments, the bristles 35 are used to brush the user's teeth and gums when the U-shaped member 11 is placed in the user's mouth.

The module 10 includes a vibration producing means used to produce the ultrasonic waves and a connecting means to transmit the waves to the U-shaped member 11. In the preferred embodiment, the vibration producing means is similar to vibration producing means commonly used in ultrasonic toothbrushes found in the prior art and now incorporated herein. Such components normally include a T-shaped member 40 longitudinally aligned inside an elongated, C-shaped frame 44. A transversely aligned pin 42 is used to pivotally interconnect the T-shaped member 40 to the C-shaped frame 44. The T-shaped member 40 extends through a stem 32 located between the frame 44 and the U-shaped member 12. The proximal end of the T-shaped member 40 is securely attached to the U-shaped member 12. Attached to the distal end of the T-shaped member 40 is a pair of opposite polarized magnets 47. During use, the magnets 47 move back and forth via set of magnets (not shown) located in the hand piece 60. Disposed longitudinally around the frame 44 is an outer, closed, cylindrical-shaped housing 50. The housing 50, the position and strength of the magnets 47, and the shape and length of the T-shaped member 40 are designed so that the module 10 may be used with currently available ultrasonic hand pieces 60, such as SONICARE sold by Optiva, Corporation of Bellevue, Wash., and SENSONIC, sold by Teledyne Waterpick Company of Fort Collins, Colo. By designing the module 10 to be used with such hand pieces 60, the module 10 may be used as an adjunct to the other brush head modules.

Attached or integrally formed on the distal end of the T-shaped member 40 is a flexible stem 32 which acts as a connecting means to connect the vibration producing means to the U-shaped element 12. Formed on the lower section of the stem 32 is a flexible seal 38 that prevents water or moisture from entering the housing 50 during use when the T-shaped member 40 moves back and forth therein.

Figure 7:
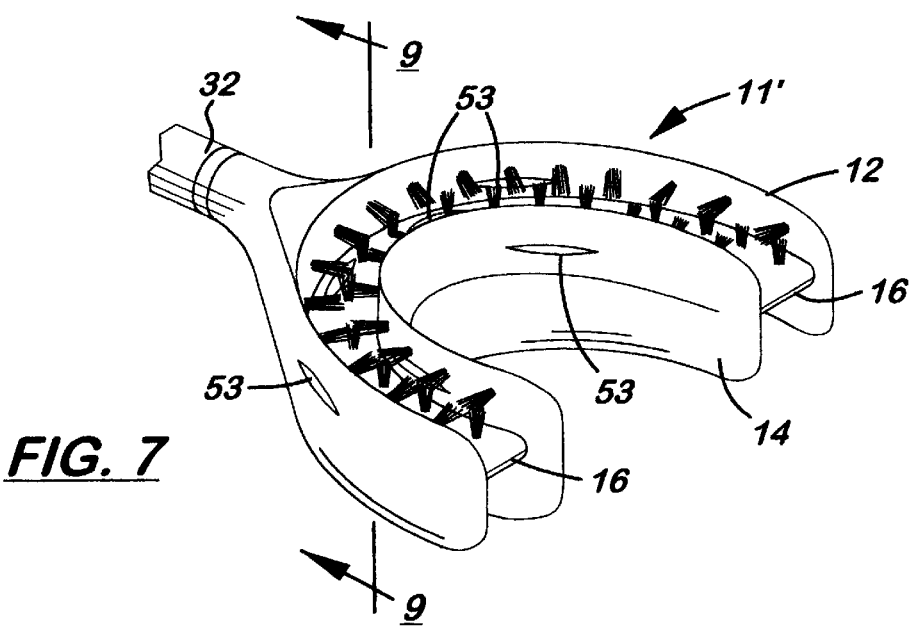
FIG. 7 is a perspective view of a second embodiment of the U-shaped member.
Figure 8:
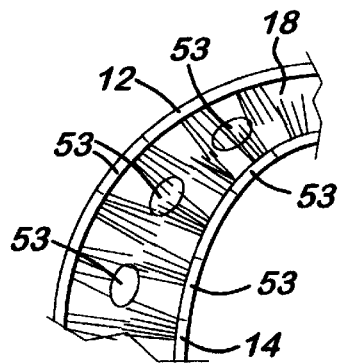
FIG. 8 is a sectional, top plan view of the U-shaped member taken along line 8—8 in FIG. 7.

Shown in FIGS. 7 and 8 is a second embodiment of the U-shaped member 11' showing a plurality of drain holes 53 formed on the U-shaped elements 12, 14 and on the flange member 16. During use, the drain holes 53 allow toothpaste and saliva to flow between and around the upper and lower bridges.

FIG. 8 is a top plan view of a section of the U-shaped member 11 showing the U-shaped members 12 and 14 having slightly different shapes so that the upper and lower bridge receiving spaces 18, 24 formed therebetween better conform to the width of the teeth and the width between the mouth's bridges for better cleaning action.

Figure 9:
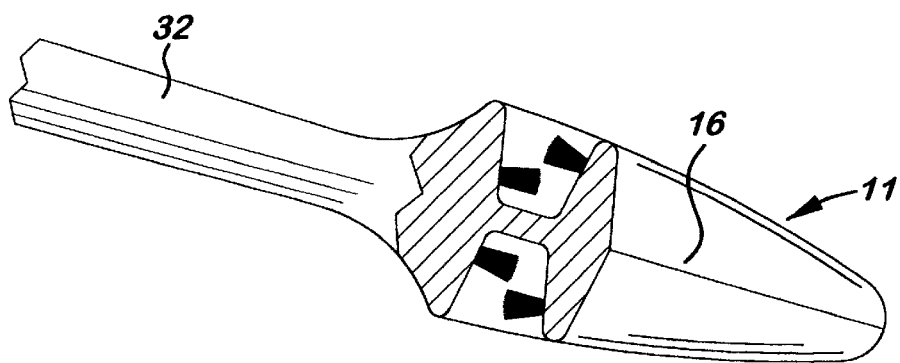
FIG. 9 is a side elevational view of a section of the U-shaped member showing the narrowing and widening of the bridge spaces.

FIG. 9 is a sectional, side elevational view taken along line 9—9 in FIG. 7 showing the tufts of bristles 35 being aligned in an upward or downward orientation on the outer and inner U-shaped elements 12, 14, respectively, so that the tips of the bristles 35 may better penetrate the gum lines and tooth pockets.

Figure 10:
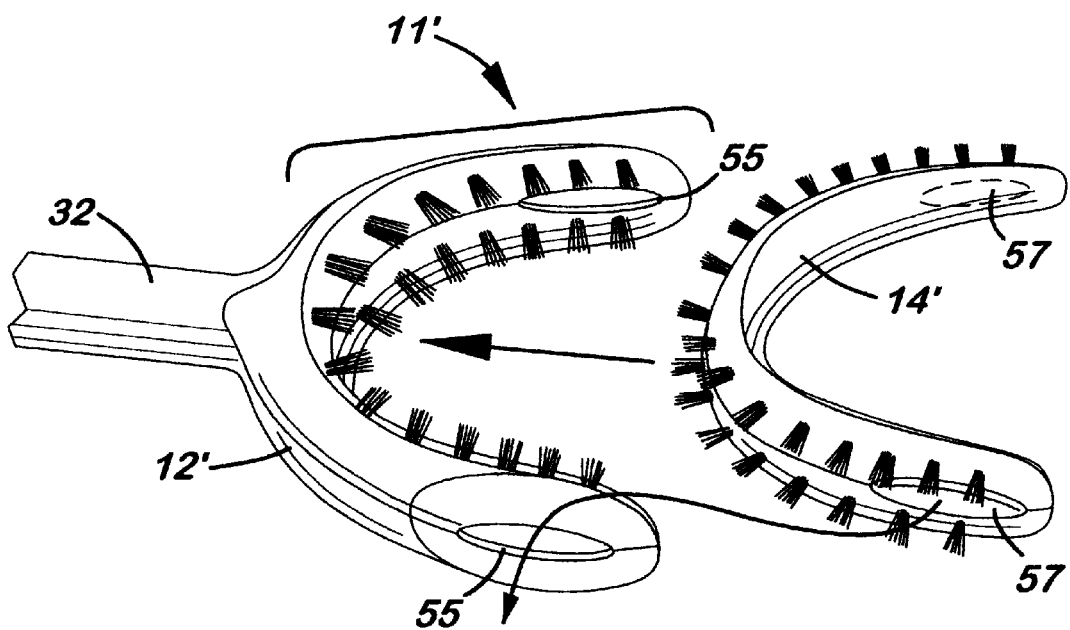
FIG. 10 is a perspective view of a third embodiment of the U-shaped member.

In FIG. 10, the second embodiment of the U-shaped member 11' is shown comprising the outer U-shaped element 12' and inner U-shaped element 14' being separated parts that snap-fit together. Formed on the outer U-shaped element 12' are slots 55 designed to receive complementary-shaped tabs 57 formed on the outer surface of the inner U-shaped element 14'. No flange member is provided on U-shaped member 11'.

Figure 11:
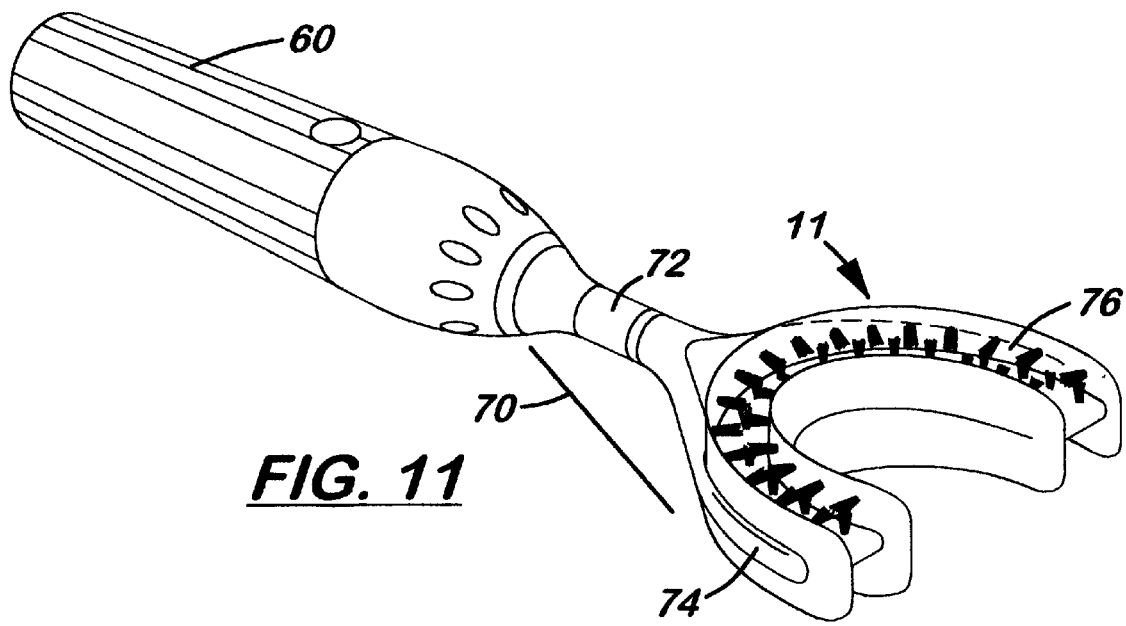
FIG. 11 is a perspective view of a fourth embodiment of the U-shaped member.

FIG. 11 shows the stem 32 replaced with a rigid Y-shaped yoke member 70 disposed around the outer surface of the outer U-shaped element 12. The central leg 72 of the yoke member 70 is attached or formed on the distal end of the T-shaped member 40 while the opposite side arms 74, 76 extend around and connect continuously to the outer surface of the outer U-shaped element 12. During use, the yoke member 70 vibrates to move the entire U-shaped member 11 inside the mouth for improved cleaning action.

In compliance with the statute, the invention described herein has been described in language more or less specific as to structural features. It should be understood, however, that the invention is not limited to the specific features shown, since the means and construction shown, comprised only of the preferred embodiments for putting the invention into effect. The invention is therefore claimed in any of its forms or modifications within the legitimate and valid scope of the amended claims, appropriately interpreted in accordance with the doctrine of equivalents.

I claim:

1. An ultrasonic toothbrush module, for use with an ultrasonic toothbrush head, comprising:

a. a U-shaped member, including opposite upper and lower bridge receiving spaces formed therein;

b. a plurality of bristles attached inside each said bridge receiving space so that when said U-shaped member is placed in a user's mouth and the user's teeth are placed in said upper and lower bridge receiving spaces, said bristles surround all of the teeth on the upper and lower bridges; and, c. means for connecting said U-shaped member to an ultrasonic toothbrush head.

2. The toothbrush module as recited in claim 1, further including drain holes in said U-shaped member to allow fluid to flow through said upper and lower bridge receiving spaces.

3. The toothbrush module as recited in claim 1, wherein said U-shaped member includes an outer U-shaped element and a longitudinal aligned and registered inner U-shaped element.

4. The toothbrush module as recited in claim 1, wherein said outer U-shaped element and said inner U-shaped element are integrally formed together.

5. The toothbrush module, as recited in claim 3, wherein said outer U-shaped element and said inner U-shaped element are separate components connected together to make said U-shaped member.

6. The toothbrush module, as recited in claim 1, further including a rigid Y-shaped member disposed around said U-shaped member to improve the transmission of vibrating movement from the ultrasonic toothbrush head to the entire length of said U-shaped member.

7. The toothbrush module, as recited in claim 1, wherein said bristles are disposed inside said bridge spaces at a non-perpendicular angle to the front and rear surface of the user's teeth when said U-shaped member is placed around the user's teeth.

8. The toothbrush module, as recited in claim 1, further including a vibration producing means capable of being connected to a hand piece having means to activate said vibration producing means.

* * * * *